United States Patent [19]

Cragoe, Jr. et al.

[11] 3,991,106
[45] Nov. 9, 1976

[54] 16-ETHERS OF 8-AZA-9-DIOXOTHIA-11,12-SECO-PROSTAGLANDINS

[75] Inventors: Edward J. Cragoe, Jr., Lansdale; James H. Jones, Blue Bell, both of Pa.

[73] Assignee: Merck & Co., Inc., Rahway, N.J.

[22] Filed: Sept. 13, 1974

[21] Appl. No.: 505,445

[52] U.S. Cl............................ 260/519; 260/558 H; 260/294.8 C; 260/470; 260/251 R; 260/347.8; 260/516; 260/332.2 A; 260/556 R; 260/561 A; 260/348 R; 424/309; 424/311; 424/320; 424/324; 424/263; 424/256; 424/275; 424/285

[51] Int. Cl.² ........................................ C07C 63/50
[58] Field of Search............. 260/519, 534 M, 534 S

[56] References Cited
UNITED STATES PATENTS
3,541,130  11/1970  Koppe et al. ........................ 260/519
3,793,365  2/1974  Winter et al. ........................ 260/519

OTHER PUBLICATIONS

Finar; I. L., *Organic Chemistry,* vol. I, (1963), Pub. by Richard Clay & Co. pp. 74, 251 & 312 relied on.

*Primary Examiner*—James O. Thomas, Jr.
*Assistant Examiner*—James H. Reamer
*Attorney, Agent, or Firm*—Thomas E. Arther; Harry E. Westlake, Jr.; Rudolph J. Anderson, Jr.

[57] ABSTRACT

The invention is concerned with novel 16-aryloxy-, 16-alkoxy-, 16-arylthio- and 16-alkylthio-8-aza-9-dioxothia-11,12-seco-prostaglandins and processes for their preparation. These novel compounds are useful as pharmaceuticals since they can be used in animals for estrus synchronization and treatment of infertility due to persistence of luteal function.

8 Claims, No Drawings

16-ETHERS OF 8-AZA-9-DIOXOTHIA-11,12-SECO-PROSTAGLANDINS

SUMMARY OF INVENTION

This invention relates to novel 16-aryloxy-, 16-alkoxy-, 16-arylthio- and 16-alkylthio-8-aza-9-dioxothia-11,12-seco-prostaglandins. These compounds can be represented by the following structural formula:

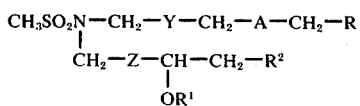

wherein R is selected from the group consisting of carboxy and a carboxy salt being formed from a pharmaceutically acceptable cation, such as metal cations derived from alkali metals, alkaline earth metals and amines such as ammonia, primary and secondary amines, and quaternary ammonium hydroxides. Especially preferred metal cations are those derived from alkali metals, e.g., sodium, potassium, lithium, and the like and alkaline earth metals, e.g., aluminum, iron and zinc.

Pharmaceutically acceptable cations derived from primary, secondary, tertiary amines, or quaternary ammonium hydroxides are methylamine, dimethylamine, trimethylamine, ethylamine, N-methylhexylamine, benzylamine, α-phenethylamine, ethylenediamine, piperidine, morpholine, pyrrolidine, 1-methylpiperazine, 1,4-dimethylpiperazine, ethanolamine, diethanolamine, triethanolamine, tris(hydroxymethyl)-aminomethane, N-methylglucamine, N-methylglucosamine, ephedrine, procaine, tetramethylammonium hydroxide, tetraethylammonium hydroxide, benzyltrimethylammonium and the like.

R is also selected from alkoxycarbonyl (—COOAlk) wherein Alk is alkyl having 1–10 carbon atoms, carbamoyl (—CONH$_2$); substituted carbamoyl (—CONR$^3$R$^4$) wherein R$^3$ and R$^4$ are selected from the group consisting of hydrogen, lower alkyl having 1–4 carbon atoms and diloweralkylaminoalkyl having 4–7 carbon atoms; and carbazoyl (—CONHNH$_2$).

R$^1$ is hydrogen or lower alkanoyl.

A is selected from the group consisting of methylene (—CH$_2$—) or oxygen (—O—).

Y is selected from the group consisting of ethylene, vinylene (particularly cis-vinylene), or ethynylene.

Z is selected from the group consisting of ethylene, vinylene (particularly trans-vinylene) or ethynylene.

R$^2$ is —O—R$^5$ or —S—R$^5$ wherein R$^5$ is lower alkyl such as ethyl, propyl, butyl and the like, fluorinated lower alkyl, such as 3,3,3-trifluoropropyl, 2,2,2-trifluoroethyl, 4,4,4-trifluorobutyl and the like, phenyl, and substituted phenyl, i.e.,

where X is halogen, trifluoromethyl, lower alkyl, lower alkoxy, dimethylamino, nitro, mesyl, lower alkanoyl and the like attached o, m or p and n is 1 or 2, and when n is 2, X$_n$ may represent such groups as methylenedioxy, benzyl or substituted benzyl,

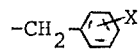

where X is as previously defined, or pyridyl, pyrimidinyl, furfuryl, thenyl and the like.

BACKGROUND OF THE INVENTION

The compounds of formula I are described as 11,12-seco-prostaglandins because of their structural relationship to the naturally occurring prostaglandins.

The prostaglandins constitute a biologically prominent class of naturally occurring, highly functionalized C$_{20}$ fatty acids which are anabolized readily in a diverse array of mammalian tissues from three essential fatty acids; namely, 8,11,14-eicosatrienoic acid, 5,8,11,14-eicosatetraenoic acid and 5,8,11,14,17-eicosapentaenoic acid. Each known prostaglandin is a formal derivative of the parent compound, termed "prostanoic acid"; the latter is a C$_{20}$ fatty acid covalently bridged between carbons 8 and 12 such as to form a trans, vicinally substituted cyclopentane in which the carboxy-bearing side chain is "alpha" or below the plane of the ring and the other side chain is "beta" or above the plane of the ring as depicted in formula III:

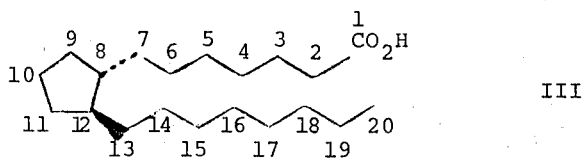

The six known primary prostaglandins, PGE$_1$, PGE$_2$, PGE$_3$, PGF$_{1\alpha}$, PGF$_{2\alpha}$, and PGF$_{3\alpha}$ resulting directly from anabolism of the above cited essential fatty acids via the action of prostaglandin synthetase, as well as the three prostaglandins resulting from in vivo dehydration of the PGE's, i.e., PGA$_1$, PGA$_2$, and PGA$_3$, are divided into three groups; namely, the PGE, PGF, and PGA series on the basis of three distinct cyclopentane nuclear substitution patterns as illustrated as follows:

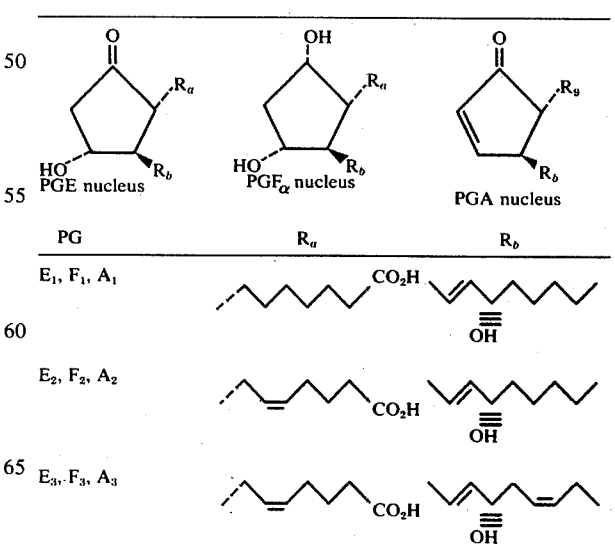

-continued

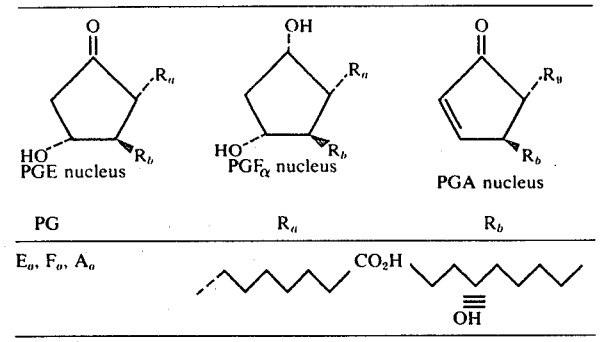

| PG | $R_a$ | $R_b$ |
|---|---|---|
| $E_a, F_a, A_a$ | ~~~~CO₂H | ~~~~~OH (with ≡) |

It should be noted that the Arabic subscripts designate the number of carbon-carbon double bonds in the designated compound and that the Greek subscript used in the PGF series designates the stereochemistry of the C–9 hydroxyl group.

Although the prostaglandins were discovered independently in the mid-1930's by Goldblatt [J. Chem. Soc. Chem. Ind. Lond., 52, 1056 (1933)] in England and Von Euler [Arch. Exp. Path. Pharmark., 175, 78 (1934)] in Sweden, these complex natural products received little attention from the scientific community until the early 1960's which coincides with the advent of modern instrumentation (e.g., mass spectrometry) which, in turn, was requisite for their successful isolation and structural elucidation by Bergström and colleagues [see Angew. Chem. Int. Ed., 4, 410 (1965) and references cited therein for an account of this work]. Within the last decade, a massive international scientific effort has been expended in developing both biosynthetic and chemical routes to the prostaglandins and, subsequently, in investigating of their biological activities. During this period, prostaglandins have been shown to occur extensively in low concentrations in a myriad of mammalian tissues where they are both rapidly anabolized and catabolized and to exhibit a vast spectrum of pharmacological activities including prominent roles in (a) functional hyperemia, (b) the inflammatory response, (c) the central nervous system, (d) transport of water and electrolytes, and (e) regulation of cyclic AMP. Further details concerning the prostaglandins can be found in recent reviews of their chemistry [J. E. Pike, Fortschr. Chem. Org. Naturst., 28, 313 (1970) and G. F. Bundy, A. Rep. in Med. Chem., 7, 157 (1972)], biochemistry [J. W. Hinman, A. Rev. Biochem., 41, 161 (1972)], pharmacology [J. R. Weeks, A. Rev. Pharm., 12, 317 (1972)], physiological significance [E. W. Horton, Physiol. Rev., 49, 122 (1969)] and general clinical application [J. W. Hinman, Postgrad. Med. J., 46, 562 (1970)].

The potential application of natural prostaglandins as medicinally useful therapeutic agents in various mammalian disease states is obvious but suffers from three formidable major disadvantages, namely, (a) prostaglandins are known to be rapidly metabolized in vivo in various mammalian tissues to a variety of metabolites which are devoid of the desired original biological activities, (b) the natural prostaglandins are inherently devoid of biological specificity which is requisite for a successful drug, and (c) although limited quantities of prostaglandins are presently produced by both chemical and biochemical processes, their production cost is extremely high; and, consequently, their availability is quite restricted.

Our interest has, therefore, been to synthesize novel compounds structurally related to the natural prostaglandins but with the following unique advantages: (a) simplicity of synthesis leading to low cost of production; (b) specificity of biological activity which may be either of a prostaglandin-mimicking or prostaglandin-antagonizing type; (c) enhanced metabolic stability. The combination of these advantages serves to provide effective, orally and parenterally active therapeutic agents for the treatment of a variety of human and animal diseases. Included are applications in renal, cardiovascular, gastrointestinal, respiratory, and reproductive systems, and in the control of lipid metabolism, inflammation, blood clotting, skin diseases, growth hormone release, selected cancers, and certain autoimmune diseases.

More specifically, in the clinic, prostaglandin agonists can function as agents for improving renal function (e.g., renal vasodilation), antihypertensives, antiulcer agents, agents for fertility control, antithrombotics, antiasthmatics, antilipolytics, antineoplastic agents, agents for the treatment of certain skin diseases, drawfism, and autoimmune diseases.

Prostaglandin antagonists can function as antiinflammatory agents, anti-diarrheal agents, antipyretics, agents for prevention of premature labor, and agents for the treatment of headache.

The compounds of this invention are particularly useful in the area of fertility control. In animals, they can be used for estrus synchronization, and treatment of infertility due to persistence of luteal function. In humans, they can be used as postcoital contraceptive agents which function by induction of menses.

Further, the compounds of this invention by virtue of their marked activity in inhibiting the aggregation of blood platelets are of potential usefulness as antithrombotic agents.

The compounds of this invention can be administered either topically or systemically, i.e., intravenously, subcutaneously, intramuscularly, orally, rectally, or by aerosolization in the form of sterile implants for long action. They can be formulated in any of a number of pharmaceutical compositions and non-toxic carriers to this end.

The pharmaceutical compositions can be sterile injectable suspensions or solutions, or solid orally administrable pharmaceutically acceptable tablets or capsules; the compositions can also be intended for sublingual administration, or for suppository use. It is especially advantageous to formulate compositions in dosage unit forms for ease and economy of administration and uniformity of dosage. "Dosage unit form" as a term used herein refers to physically discrete units suitable as unitary dosages for animal and human subjects, each unit containing a predetermined quantity of active material calculated to produce the desired biological effect in association with the required pharmaceutical means.

Illustratively, a sterile injectable composition can be in the form of aqueous or oleagenous suspensions or solutions.

The sterile injectable composition can be aqueous or oleagenous suspension or solution. Suspensions can be formulated according to the known art using suitable dispersing and wetting agents and suspending agents. Solutions are similarly prepared from the salt form of the compound. For the laboratory animals, we prefer to use incomplete Freund's adjuvant or sterile saline (9%) as carrier. For human parenteral use, such as intramuscularly, intravenously, or by regional perfusion, the diluent can be a sterile aqueous vehicle containing a preservative; for example, methylparaben, propylparaben, phenol, and chlorobutanol. The aqueous vehicle can also contain sodium chloride, preferably in an amount to be isotonic; as well as a suspending agent, for example, gum arabic, polyvinyl pyrrolidone, methyl cellulose, acetylated monoglyceride (available commercially as Myvacet from Distillation Products Industry, a division of Eastman Kodak Company), monomethyl glyceride, dimethyl glyceride or a moderately high molecular weight polysorbitan (commercially available under the tradenames Tween or Span from Atlas Powder Company, Wilmington, Delaware). Other materials employed in the preparation of chemotherapeutic compositions containing the compound may include glutathione, 1,2-propanediol, glycerol and glucose. Additionally, the pH of the composition is adjusted by use of an aqueous solution such as tris(hydroxymethyl)aminomethane (tris buffer).

Oily pharmaceutical carriers can also be used, since they dissolve the compound and permit high doses. Many oily carriers are commonly employed in pharmaceutical use, such as, for example, mineral oil, lard, cottonseed oil, peanut oil, sesame oil, or the like.

It is preferred to prepare the compositions, whether aqueous or oils, in a concentration in the range of from 2-50 mg./ml. Lower concentrations require needless quantities of liquid. Higher concentrations than 50 mg./ml. are difficult to maintain and are preferably avoided.

Oral administration forms of the drug can also be prepared for laboratory animals or human patients. The same dosage levels can be used as for injectable forms. Generally, a solid unit dosage form can be prepared containing from 0.5 mg. to 25 mg. active ingredient.

Whatever the mode of administration, doses in the range of about 0.10 to 20 milligrams per kilogram of body weight administered one to four times per day are used, the exact dose depending on the age, weight, and condition of the patient, and the frequency and route of administration.

The low cost and ready accessibility of the compounds of this invention make them particularly promising for applications in veterinary medicine. In particular, their luteolytic properties make them useful as agents for estrus synchronization in cattle, horses and other farm animals.

METHODS

Two general methods are employed for the preparation of those compounds of formula I where R is carboxy, and $R^1$ is hydrogen, all other symbols being defined as before.

Method A

This method is used for preparation of compounds of formula II: where $R^2$ is as defined previously.

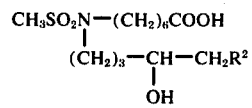

(1) Methanesulfonamide is converted to its anion by means of a strong base (sodium hydride, potassium tert-butoxide, etc.) in a solvent such as dimethylformamide or dimethylformamide-benzene, and then alkylated with halide III:

$$X-(CH_2)_6-COOR^6 \qquad \text{III}$$

where $R^6$ is straight chain lower alkyl, preferably methyl or ethyl and X is halogen (chloro, bromo, or iodo). The product is IV.

$$CH_3SO_2NH-(CH_2)_6COOR^6 \qquad \text{IV}$$

(2) Compound IV is converted to its anion in like manner and alkylated with the halo-olefin V:

$$X-(CH_2)_3CH=CH_2 \qquad \text{V}$$

where X is halogen (chloro, bromo, or iodo) to give the product VI.

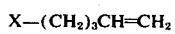

(3) Compound VI is converted to the epoxide VII by treatment with a suitable peroxide compound (peracetic acid, m-chloroperbenzoic acid) in an inert solvent (methylene chloride) at temperatures from 0°–35°C. The epoxide obtained is VII.

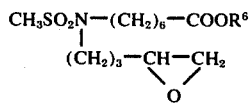

(4) Epoxide VII is treated in a solvent or solvent system such as dimethylformamide, dimethylformamide-benzene, tetrahydrofuran and the like, with the anion derived from an alcohol, phenol, or mercaptan $R^5OH$ or $R^5SH$. Such anion is obtained by addition of a suitable base (sodium hydride, potassium t-butoxide, etc.) to a solution of $R^5OH$ or $R^5SH$ in the above solvent system. Attack of $R^5O^-$ or $R^5S^-$ on VII yields compound VIII:

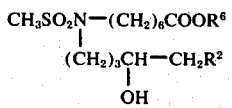

where $R^2$ and $R^6$ are as previously defined. Note VIII is a product of this invention.

(5) The ester VIII is hydrolyzed in dilute aqueous alkaline solution (preferably sodium or potassium hydroxide in aqueous methanol or ethanol) at temperatures of 25°–70° C. to give the products of the invention II.

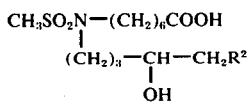

Steps 4 and 5 can be combined in a single process where epoxide VII is treated in an aqueous system (tetrahydrofuran-water, dimethyl sulfoxide-water, etc.) with sodium or potassium hydroxide and $R^5OH$ or $R^5SH$. Epoxide opening and ester hydrolysis occur simultaneously to yield product II.

Method B

This method is used for preparation of compounds of formula IX:

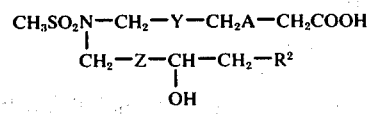

where A, Y, Z and $R^2$ are as defined previously. (1) Methanesulfonamide is converted to its anion as above and alkylated with halide X:

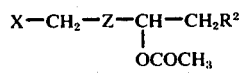

to give the intermediate XI where Z and $R^2$ are as defined.

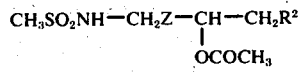

(2) Compound XI is converted to its anion as above and alkylated with halide XII.

to give the intermediate ester XIII.

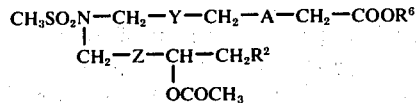

(3) Ester XIII is treated with dilute aqueous base in a suitable solvent (sodium or potassium hydroxide in aqueous methanol or ethanol) at temperatures of 25°–70° C. for 12–24 hours to effect ester hydrolysis and yield the products of the invention IX.

Further Products of the Invention

1. The fundamental processes yield compounds where R is carboxy. To obtain carboxy salts the acid products are dissolved in a solvent such as ethanol, methanol, glyme and the like and the solution treated with an appropriate alkali or alkaline earth hydroxide or alkoxide to yield the metal salt, or with an equivalent quantity of ammonia, amine or quaternary ammonium hydroxide to yield the amine salt. In each instance, the salt either separates from the solution and may be separated by filtration or, when the salt is soluble it may be recovered by evaporation of the solvent. Aqueous solutions of the carboxylic acid salts can be prepared by treating an aqueous suspension of the carboxylic acid with an equivalent amount of an alkaline earth hydroxide or oxide, alkali metal hydroxide, carbonate or bicarbonate, ammonia, an amine or a quaternary ammonium hydroxide.

To obtain carboxy esters (i.e., compounds where R is COOAlk) the acid products are treated in ether with an ethereal solution of the appropriate diazoalkane. For example, methyl esters are produced by reaction of the acid products with diazomethane. To obtain products where R is carbamoyl, substituted carbamoyl or carbazoyl the acid product is first converted to an active Woodward ester. For example, the acid product can be made to react with N-tert-butyl-5-methylisoxazolium perchlorate in acetonitrile in the presence of a base such as triethylamine to yield an active ester in which R is

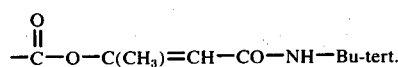

Active esters of this type can be reacted with ammonia to yield products of formula I where R is carbamoyl, with primary or secondary amines or di-loweralkylaminoalkylamines to yield products where R is substituted carbamoyl, i.e., $-CONR^3R^4$, and with hydrazine to yield products where R is carbazoyl.

2. The fundamental processes yield products where $R^1$ is hydrogen. In compounds containing no additional hydroxy group and in which $R^1$ is hydrogen, reaction with formic acid, acetic anhydride, propionic anhydride, butyric anhydride, isobutyric anhydride, valeric anhydride, pivalic anhydride and the like, without solvent and at temperatures from 25° to 60° C., gives compounds wherein $R^1$ is formyl, acetyl, propionyl, butyryl, isobutyryl, valeryl, and pivaloyl, respectively.

3. Compounds where Y is cis-vinylene can be prepared from products of the invention where Y is ethynylene by hydrogenation in the presence of the Lindlar catalyst.

Preparation of Intermediates

1. Methods for the preparation of the halides III, V and XII have been described in the literature.

2. Varied methods are used for the preparation of the halides X.

a. When Z is ethynylene these intermediates can be represented by formula Xa.

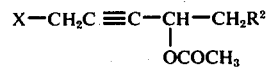

The preparation of Xa is as follows:

Phenol or thiophenol, $R^5OH$ or $R^5SH$, is treated with base (sodium hydride, potassium-t-butoxide, etc.) in suitable solvent (DMF, t-butanol) and then made to react with bromoacetaldehyde diethyl (or dimethyl) acetal to give $R^2CH_2CH(OC_2H_5)_2$. This acetal is hydrolyzed in aqueous acidic medium preferably at 80°–120° to give the substituted acetaldehyde $R^2CH_2CHO$. The acetaldehyde is treated with the acetylenic Grignard reagent prepared from tetrahydro-2-(2-propynyloxy)-2H-pyran (THP-OCH$_2$C≡CH, where THP = 2-tetrahydropyranyloxy) to give after workup the acetylenic alcohol THP—O—CH$_2$—C≡C—CHOH—CH$_2$—R$^2$. This alcohol is acetylated preferably with acetic anhydride in pyridine to yield THP—O—CH$_2$C≡C—CH(OCOCH$_3$)—CH$_2$—R$^2$. The tetrahydropyranyl protecting group is hydrolyzed in aqueous acidic medium to yield primary acetylenic alcohol HOCH$_2$C≡C—CH(OCOCH$_3$)CH$_2$R$^2$. Treatment of this alcohol with phosphorus tribromide in ether at 10°–35° yields BrCH$_2$C≡C—CH(OCOCH$_3$)CH$_2$—R$^2$, a compound of formula X$a$ where X = Br.

b. When Z is trans-ethylene, the intermediates XIV can be represented by formula X$b$.

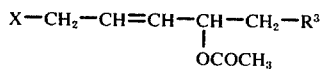
                                                            X$b$

The preparation of X$b$ begins with the protected acetylenic alcohol, THPOCH$_2$C≡C—CHOH—CH$_2$R$^2$, used in the preparation of X$a$. In this case, the acetylenic alcohol is reduced with lithium aluminum hydride in a suitable solvent such as ether or tetrahydrofuran to give the trans olefinic alcohol THP—O—CH$_2$CH=CH—CHOH—CH$_2$—R$^2$. The alcohol is acetylated preferably with acetic anhydride in pyridine to yield THP—O—CH$_2$—CH=CH—CH(OCOCH$_3$)—CH$_2$—R$^2$. The tetrahydropyranyl group is hydrolyzed in aqueous acidic medium to yield HOCH$_2$CH=CH—CH(OCOCH$_3$)—CH$_2$R$^2$. This alcohol can be converted to the halide X$b$ by a variety of procedures. For example, the alcohol on treatment with phosphorus tribromide in ether gives X$b$ where X is bromo. Or, the alcohol can be treated with p-toluenesulfonyl chloride in piperidine to obtain the tosylate which can be made to react with sodium iodide in acetone to yield X$b$ where X is iodo.

c. When Z is ethylene, the intermediates X can be represented by formula X$c$.

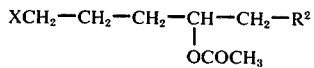
                                                              X$c$

The preparation of X$c$ begins with the protected acetylenic acetate, THP—O—CH$_2$C≡C—CH(OCOCH$_3$)—CH$_2$—R$^2$, used in the preparation of X$a$. Here, this compound is hydrogenated preferably over a palladium catalyst in an aprotic solvent at 1–4 atmospheres and 20°–40°. The saturated compound THP—O—(CH$_2$)$_3$—CH(OCOCH$_3$)—CH$_2$—R$^2$ is obtained. The tetrahydropyranyl group is hydrolyzed in aqueous acidic medium to give HO—(CH$_2$)$_3$—CH(OCOCH$_3$)—CH$_2$—R$^2$. This alcohol is treated with P-toluenesulfonyl chloride in pyridine to yield the tosylate which when treated with sodium iodide in acetone undergoes metathesis to yield I—(CH$_2$)$_3$—CH(OCOCH$_3$)—CH$_2$—R$^2$ which is a compound of formula X$c$ where X = iodo.

EXAMPLE 1

Preparation of 7-{N-[4-Hydroxy-5-(4-fluorophenoxy)pentyl]-methanesulfonamido}heptanoic Acid Step A: Preparation of Ethyl 7-(methanesulfonamido)heptanoate A stirred suspension of sodium hydride (57% in mineral oil) (2.33 g., 0.055 mole) in a solvent mixture of benzene (50 ml.) and dimethylformamide (50 ml.) is treated, over 30 minutes, with methanesulfonamide (4.75 g., 0.055 mole). This mixture is heated on the steam bath for 1.5 hours, then cooled to room temperature. At this temperature is added ethyl 7-bromoheptanoate (13 g., 0.055 mole) and the reaction mixture is heated at 90° C. for 20 hours. The reaction is poured into ater (200 ml.), neutralized with hydrochloric acid and extracted with ethyl acetate (2 × 100 ml.). The ethyl acetate layer is washed with brine, dried over sodium sulfate, then concentrated in vacuo. The yield of ethyl 7-(methanesulfonamido)heptanoate is 7.1 g. (51%) boiling 165°–168°/0.1 mm.

Anal. Calcd. for C$_{10}$H$_{21}$NO$_4$S: C, 47.78; H, 8.42; N, 5.57; Found: C, 47.05; H, 8.51; N, 5.41.

Step B: Preparation of Ethyl 7-[N-(5-penten-1-yl)methanesulfonamido]-heptanoate

A stirred suspension of sodium hydride (57% in mineral oil) (750 mg., 0.0176 mole) in a solvent mixture of benzene (50 ml.) and dimethylformamide (50 ml.) is treated, over 30 minutes, with ethyl 7-(methanesulfonamido)-heptanoate (4.18 g., 0.016 mole) dissolved in dimethylformamide (10 ml.). This mixture is heated on the steam bath for 30 minutes, then cooled to room temperature. At this temperature is added 5-bromo-1-pentene (2.62 g., 0.0176 mole) and the reaction is heated at 90° C. for 20 hours. The reaction is poured into water (200 ml.), neutralized with hydrochloric acid and extracted with ethyl acetate (2 × 100 ml.). The ethyl acetate layer is washed with brine, dried over sodium sulfate, then concentrated in vacuo. The yield of ethyl 7-[N-(5-penteneyl)methanesulfonamido]heptanoate is 3.2 g. (60%) boiling 177°–185°/0.1 mm.

Anal. Calcd. for C$_{15}$H$_{29}$NO$_4$S: C, 56.39; H, 9.15; N, 4.38; Found: C, 57.01; H, 9.30; N, 4.19.

Step C: Preparation of Ethyl 7-[N-(4,5-epoxypentyl)-methanesulfonamido]heptanoate A solution of m-chloroperbenzoic acid (2.24 g., 0.013 mole) in methylene chloride (50 ml.) is added dropwise to ethyl 7-[N-(5-penten-1-yl)methanesulfonamido]-heptanoate (3.8 g., 0.012 mole) in methylene chloride (50 ml.) at room temperature. This solution is heated at reflux for one hour then cooled and washed with 5% sodium bicarbonate till the wash is slightly basic. The organic phase is dried over sodium sulfate then evaporated in vacuo. The resulting oil is purified by chromatography over silica gel using chloroform to elute. Evaporation of the appropriate fractions affords the subject compound. The yield is 2.3 g. (57%) of pale yellow oil.

Anal. Calcd. for C$_{15}$H$_{29}$NO$_5$S: C, 53.71; H, 8.72; N, 4.18; Found: C, 53.38; H, 9.13; N, 4.16.

Step D: Preparation of Ethyl 7-{N-[4-hydroxy-5-(4-fluorophenoxy)pentyl]methanesulfonamido}heptanoate To a stirred suspension of sodium hydride (57%) (278 mg., 0.0065 mole) in a solvent mixture of benzene (25 ml.) and dimethylformamide (25 ml.) is added, over 30 minutes, a solution of p-fluorophenol (730 mg., 0.065 mole) in dimethylformamide (10 ml.). This mixture is stirred 30 minutes at room temperature, then treated with a solution of ethyl 7-[N-(4,5-epoxypentyl)methanesulfonamido]heptanoate (2.2 g., 0.0065 mole) in benzene (10 ml.). The reaction is heated at 90° C. for eighteen hours, then cooled and poured into water (100 ml.). The organic phase is collected, washed with brine and dried over sodium sulfate. Evaporation in vacuo affords a heavy oil that is purified by chromatography over silica gel, using chloroform to elute. Evaporation of the appropriate fractions affords the subject compound. The yield is 1.4 g. (47%) of heavy oil.

Anal. Calcd. for $C_{21}H_{34}FNO_6S$: C, 56.35; H, 7.66; N, 3.13; Found: C, 56.17; H, 7.75; N, 3.22.

Step E: Preparation of 7-{N-[4-hydroxy-5-(4-fluorophenoxy)-pentyl]methanesulfonamido}heptanoic acid A solution composed of ethyl 7-{N-[4-hydroxy-5-(4-fluorophenoxy)pentyl]methanesulfonamido}heptanoate (4.7 g., 0.11 mole), sodium hydroxide (1.0 g.), water (13 ml.) and ethanol (130 ml.) is kept at room temperature for 20 hours. Most of the solvent is removed in vacuo, water (150 ml.) is added and the solution extracted with ether (100 ml.). The aqueous layer is acidified (hydrochloric acid) and extracted with ethyl acetate (2 × 100 ml.). The organic layer is dried over sodium sulfate then concentrated in vacuo to obtain the subject compound. The yield is 3.7 g. (84%) of heavy oil.

Anal. Calcd. for $C_{19}H_{30}FNO_6S$: C, 54.40; H, 7.21; N, 3.34; Found: C, 54.49; H, 7.30; N, 3.36.

EXAMPLE 2

Preparation of
7-{N-[4-Hydroxy-5-(4-fluorophenoxy)pentyl]-methanesulfonamido}hept-5-ynoic Acid Step A: Preparation of 4-Fluorophenoxyacetaldehyde Diethyl Acetal A solution of p-fluorophenol (28.1 g., 0.25 mole) in DMF (30 ml.) is added dropwise to a suspension of hexane (2 × 30 ml.)-prewashed sodium hydride (50% oil dispersion, 12.5 g., 0.26 mole) in DMF (120 ml.). The resulting mixture is stirred at room temperature for 10 minutes, treated with bromoacetaldehyde diethyl acetal (49.3 g., 0.25 mole), and finally heated on a steam bath for 4 hours. The reaction mixture is allowed to come to room temperature and the precipitated sodium bromide is filtered off. DMF is then removed on a rotary evaporator, the oil residue is diluted with acetone (100 ml.) and another quantity of sodium bromide is precipitated which again is removed by filtration. The filtrate is then concentrated on a rotary evaporator leaving an oil residue which is vacuum distilled at 87°/0.05 mm to yield the desired product as colorless oil (46.7 g., 0.205 mole, 82%). ir (neat) 3.4~3.5, 6.21, 6.64, 8.00, 8.25, 8.83, 9.32, 12.08, 13.20$\mu$; pmr ($CCl_4$) $\delta$ 1.17 (6H, t, J=7.5Hz), 3.57 (2H, q, J=7.5Hz), 3.61 (2H, q, J=7.5Hz), 3.85 (2H, d, J=5Hz), 4.68 (1H, t, J=5Hz), 6.6–7.1 (4H, m).

Step B: Preparation of 4-Fluorophenoxyacetaldehyde

A mixture of 4-fluorophenoxyacetaldehyde diethyl acetal (30.0 g., 0.131 mole), acetone (150 ml.), water (150 ml.), and concentrated sulfuric acid (0.8 ml.) is refluxed overnight (ca. 16 hr.). The mixture is allowed to cool to room temperature and is then extracted with methylenechloride four times. The combined extracts are washed with aqueous sodium bicarbonate and dried over anhydrous magnesium sulfate. The solvent is stripped off on a rotary evaporator and the oil residue is subsequently distilled in vacuo at 70°/0.05 mm to give the title compound (19.0 g., 0.123 mole, 94%). ir (neat) 3.23, 3.50, 3.63, 5.71, 6.62, 7.00, 8.00, 8.24, 9.07, 9.38, 12.03, 12.51, 13.12$\mu$; pmr ($CCl_4$) $\delta$ 4.37 (2H, d, J=1Hz), 6.6–7.1 (4H, m), 9.68 (1H, t, J=1Hz).

Step C: Preparation of 1-(2-Tetrahydropyranyloxy)-4-acetoxy-5-(4-fluorophenoxy)-2-pentyne To the Grignard reagent prepared from magnesium (11.58 g.; 0.476 mole) and bromoethane (51.88 g.; 0.476 mole) in tetrahydrofuran (400 ml.) is added, dropwise, during 30 minutes, a solution of tetrahydro-2-(2-propynyloxy)-2H-pyran (64.06 g.; 0.457 mole) in tetrahydrofuran (40 ml.). The mixture is stirred at room temperature, under nitrogen, for 1 hour, then chilled in an ice bath and treated, dropwise, during 30 minutes, with a solution of 4-fluorophenoxyacetaldehyde (61.20 g., 0.397 mole) in tetrahydrofuran (60 ml.). The mixture is heated on a steam bath, under nitrogen, for 1 hour, then again chilled in an ice bath and treated, dropwise, during 30 minutes, with a mixture of acetic anhydride (48.60 g., 0.476 mole) and pyridine (75.31 g., 0.952 mole). The mixture is heated on a steam bath, under nitrogen, for 30 minutes.

The mixture is poured into cold water (1200 ml.) and the organic layer is separated. The aqueous layer is extracted with ether. The combined organic extracts are washed with water and then dried over anhydrous magnesium sulfate. The solvent is removed under vacuum to give the title compound as an orange-red residual oil, yield 133.54 g.; pmr ($CDCl_3$) $\delta$ 2.07 (3H, s $CH_3COO$), 4.17 (2H, d $CH_2O$), 4.32 (2H, d $CH_2C\equiv C$), 5.78 (1H, m CHOCO), 6.95 (4H, m aryl H).

Step D: Preparation of 1-(2-Tetrahydropyranyloxy)-4-acetoxy-5-(4-fluorophenoxy)pentane 1-(2-Tetrahydropyranyloxy)-4-acetoxy-5-(4-fluorophenoxy)-2-pentyne (13.4 g., 0.04 mole) is dissolved in ethyl acetate (100 ml.). 5% Palladium on carbon is added and the mixture is hydrogenated on the Parr apparatus at an initial pressure of 41 lbs./in$^2$ and 25°. When 0.08 mole of hydrogen is absorbed, the catalyst is removed by filtration and the solvent is evaporated under vacuum to give the title compound as a light orange residual oil, yield 12.90 g.

Step E: Preparation of 4-Acetoxy-5-(4-fluorophenoxy)-1-pentanol

A mixture of 1-(2-tetrahydropyranyloxy)-4-acetoxy-5-(4-fluorophenoxy)pentane (143.5 g., 0.422 mole), methanol (700 ml.), concentrated hydrochloric acid (3 ml.) and ethyl acetate (70 ml.) is stirred at room temperature for 1 hour.

The reaction mixture is poured into cold $H_2O$ (1500 ml.) and the organic layer is extracted with ether. The combined extracts are washed with saturated sodium bicarbonate solution, then brine and dried over anhydrous magnesium sulfate. The solvent is removed under vacuum and the residual oil is distilled to give the title compound as a light yellow oil, yield 72.6 g. (67%), b.p. 158°–160°/0.1 mm, pmr ($CDCl_3$) $\delta$ 2.08 (3H, s $CH_3COO$), 3.65 (2H, t $HOCH_2$), 4.00 (2H, d $CH_2O$), 5.18 (1H, m CHOCO), 6.83 (4H, m aryl H).

Step F: Preparation of 4-Acetoxy-5-(4-fluorophenoxy)-1-pentanol Tosylate

A solution of p-toluenesulfonyl chloride (42.0 g., 0.22 mole) in pyridine (100 ml.) is cooled in an ice bath while 4-acetoxy-5-(4-fluorophenoxy)-1-pentanol (49.7 g., 0.193 mole) is added dropwise with stirring during 40 minutes. The ice bath is replaced by a cool (20°) water bath and stirring is continued for 2 hours. The mixture is then poured into 500 ml. of water. The oily product is taken up in ether, washed with 2N hydrochloric acid and water and dried over sodium sulfate. The solvent is distilled in vacuo to leave 73.5 g. (93%) of the crude title compound as a yellow oil.

Step G: Preparation of 4-Acetoxy-5-(4-fluorophenoxy)-1-iodopentane

A solution of 4-acetoxy-5-(4-fluorophenoxy)-1-pentanol tosylate (73.5 g., 0.179 mole) and sodium iodide (79.5 g., 0.53 mole) in acetone (500 ml.) is allowed to stand at 25°–27° for 18 hours. The precipitated sodium tosylate is filtered off. Most of the acetone is evaporated from the filtrate and the residue is treated with 300 ml. of water. The oily product is taken up in ether, washed with dilute sodium thiosulfate solution, water and brine and dried over sodium sulfate. The solvent is distilled in vacuo to give 66 g. (a quantitative yield) of the crude title compound as a yellowish oil which is used without further purification; pmr (CDCl$_3$) δ 2.05 (3H, s CH$_3$CO); 3.20 (2H, t CH$_2$I); 3.97 (2H, d CH$_2$O); 5.20 (1H, m CHO); 6.85 (4H, m aryl).

Step H. Preparation of N-[4-Acetoxy-5-(4-fluorophenoxy)-pentyl]methanesulfonamide A stirred suspension of sodium hydride (57%) (0.91 g., 0.022 mole) in a solvent mixture of benzene (50 ml.) and dimethylformamide (50 ml.) is treated, over 30 minutes, with methanesulfonamide (1.9 g., 0.02 mole). This mixture is heated on the steam bath for 1.5 hours, then cooled to room temperature. At this temperature is added 4-acetoxy-5-(4-fluorophenoxy)-1-iodopentane (8.05 g., 0.022 mole) and the reaction is heated at 90° C. for 20 hours. The reaction is poured into water (200 ml.), neutralized with hydrochloric acid and extracted with ethyl acetate (2 × 100 ml.). The ethyl acetate layer is washed with brine, dried over sodium sulfate, then concentrated in vacuo. The product is purified by chromatography over silica gel using 5% methanol in chloroform to elute. Evaporation of the appropriate fractions affords the subject compound as a pale yellow oil.

Step I: Preparation of Methyl 7-{N-[4-acetoxy-5-(4-fluorophenoxy)pentyl]methanesulfonamido}hept-5-ynoate A stirred suspension of sodium hydride (57%) (.91 g., 0.022 mole) in a solvent mixture of benzene (50 ml.) and dimethylformamide (50 ml.) is treated, over 30 minutes, with N-[4-acetoxy-5-(4-fluorophenoxy)-pentyl]-methanesulfonamide (6.5 g., 0.02 mole). This mixture is heated at 60° C. until evolution of hydrogen ceases, then cooled to room temperature. At this temperature is added methyl 7-bromo-5-heptynoate (4.3 g., 0.02 mole) and the reaction is heated at 90° C. for 3 hours. The reaction is poured into water (200 ml.), neutralized with hydrochloric acid and extracted with ethyl acetate (2 × 100 ml.). The ethyl acetate layer is washed with brine, dried over sodium sulfate, then concentrated in vacuo. The product is purified by chromatography over silica gel using 5% methanol in chloroform to elute. Evaporation of the appropriate fractions affords the subject compound as a yellow oil.

Step J: Preparation of 7-{N-[4-hydroxy-5-(4-fluorophenoxy)-pentyl]methanesulfonamido}hept-5-ynoic Acid The synthesis of this compound is carried out as described in Example 1, Step E except that the ethyl 7-{N-[4-hydroxy-5-(4-fluorophenoxy)pentyl]methanesulfonamido}-heptanoate is replaced by an equimolar amount of methyl 7-{N-[4-acetoxy-5-(4-fluorophenoxy)pentyl]methanesulfonamido}-hept-5-ynoate and the amount of sodium hydroxide is doubled. The product of this reaction is the subject compound.

Further, following the procedure of Example 2, Step A, but substituting for the p-fluorophenol used therein an equivalent quantity of
1. 3-bromophenol
2. 3-iodophenol
3. 2-chlorophenol
4. 3-methylphenol
5. 3-mesylphenol
6. 3-dimethylaminophenol
7. 3-ethylphenol
8. 3-methoxyphenol
9. 3-fluorophenol
10. 2,3-difluorophenol
11. 3,4-methylenedioxyphenol or 12. 2,4-dichlorophenol and conducting the reactions and isolations as described in Steps A through I, the product obtained in Step I in each instance is:
1. methyl 7-{N-[4-acetoxy-5-(3-bromophenoxy)pentyl]-methanesulfonamido}hept-5-ynoate
2. methyl 7-{N-[4-acetoxy-5-(3-iodophenoxy)pentyl]-methanesulfonamido}hept-5-ynoate
3. methyl 7-{N-[4-acetoxy-5-(2-chlorophenoxy)pentyl]-methanesulfonamido}hept-5-ynoate
4. methyl 7-{N-[4-acetoxy-5-(3-methylphenoxy)pentyl]-methanesulfonamido}hept-5-ynoate
5. methyl 7-{N-[4-acetoxy-5-(3-mesylphenoxy)pentyl]-methanesulfonamido}hept-5-ynoate
6. methyl 7-{N-[4-acetoxy-5-(3-dimethylaminophenoxy)pentyl]-methanesulfonamido}hept-5-ynoate
7. methyl 7-{N-[4-acetoxy-5-(3-ethylphenoxy)pentyl]-methanesulfonamido}hept-5-ynoate
8. methyl 7-{N-[4-acetoxy-5-(3-methoxphenoxy)pentyl]-methanesulfonamido}hept-5-ynoate
9. methyl 7-{N-[4-acetoxy-5-(3-fluorophenoxy)pentyl]-methanesulfonamido}hept-5-ynoate
10. methyl 7-{N-[4-acetoxy-5-(2,3-difluorophenoxy)-pentyl]-methanesulfonamido}hept-5-ynoate
11. methyl 7-{N-[4-acetoxy-5-(3,4-methylenedioxyphenoxy)-pentyl]methanesulfonamido}hept-5-ynoate
12. methyl 7-{N-[4-acetoxy-5-(2,4-dichlorophenoxy)-pentyl]-methanesulfonamido}hept-5-ynoate Then, following the procedure of Example 2, Step J, but substituting for the methyl 7-{N-[4-acetoxy-5-(4-fluorophenoxy)pentyl]methanesulfonamido}-hept-5-ynoate used therein an equivalent amount of each of the 12 esters listed above, there are obtained
1. 7-{N-[4-hydroxy-5-(3-bromophenoxy)pentyl]methanesulfonamido}hept-5-ynoic acid
2. 7-{N-[4-hydroxy-5-(3-iodophenoxy)pentyl]methanesulfonamido}hept-5-ynoic acid
3. 7-{N-[4-hydroxy-5-(2-chlorophenoxy)pentyl]methanesulfonamido}hept-5-ynoic acid
4. 7-{N-[4-hydroxy-5-(3-methylphenoxy)pentyl]methanesulfonamido}hept-5-ynoic acid
5. 7-{N-[4-hydroxy-5-(3-mesylphenoxy)pentyl]methanesulfonamido}hept-5-ynoic acid
6. 7-{N-[4-hydroxy-5-(3-dimethylaminophenoxy)pentyl]methanesulfonamido}hept-5-ynoic acid
7. 7-{N-[4-hydroxy-5-(3-ethylphenoxy)pentyl]methanesulfonamido}hept-5-ynoic acid
8. 7-{N-[4-hydroxy-5-(3-methoxyphenoxy)pentyl]methanesulfonamido}hept-5-ynoic acid
9. 7-{N-[4-hydroxy-5-(3-fluorophenoxy)pentyl]methanesulfonamido}hept-5-ynoic acid
10. 7-{N-[4-hydroxy-5-(2,3-difluorophenoxy)pentyl]methanesulfonamido}hept-5-ynoic acid 11. 7-{N-[4-hydroxy-5-(3,4-methylenedioxyphenoxy)-pentyl]-sulfonamido}hept-5-ynoic acid
12. 7-{N-[4-hydroxy-5-(2,4-dichlorophenoxy)pentyl]-methanesulfonamide}hept-5-ynoic acid

EXAMPLE 3

Preparation of
7-{N-[4-hydroxy-5-(4-fluorophenoxy)pentyl]-methanesulfonamido}cis-hept-5-enoic Acid A solution of 7-{N-[4-hydroxy-5-(4-fluorophenoxy)pentyl]methanesulfonamido}hept-5-ynoic acid in ethyl acetate is hydrogenated over Lindlar catalyst at atmospheric pressure and room temperature. One molar equivalent of hydrogen is absorbed whereupon uptake of hydrogen ceases. The catalyst is filtered off and the solvent evaporated to leave the subject compound as a residual oil.

Following the procedure of Example 3 but substituting for the 7-{N-[4-hydroxy-5-(4-fluorophenoxy)-pentyl]methanesulfonamido}hept-5-ynoic acid the 12 analogous compounds listed at the end of Example 2, and conducting the reactions and isolating the products as described in Example 3, there is obtained 1. 7-{N-[4-hydroxy-5-(3-bromophenoxy)pentyl]methanesulfonamido}-cis-hept-5-enoic acid
2. 7-{N-[4-hydroxy-5-(3-iodophenoxy)pentyl]methanesulfonamido}-cis-hept-5-enoic acid
3. 7-{N-[4-hydroxy-5-(2-chlorophenoxy)pentyl]methanesulfonamido}-cis-hept-5-enoic acid
4. 7-{N-[4-hydroxy-5-(3-methylphenoxy)pentyl]methanesulfonamido}-cis-hept-5-enoic acid
5. 7-{N-[4-hydroxy-5-(3-mesylphenoxy)pentyl]methanesulfonamido}-cis-hept-5-enoic acid
6. 7-{N-[4-hydroxy-5-(3-dimethylaminophenoxy)pentyl]-methanesulfonamido}-cis-hept-5-enoic acid
7. 7-{N-[4-hydroxy-5-(3-ethylphenoxy)pentyl]methanesulfonamido}-cis-hept-5-enoic acid
8. 7-{N-[4-hydroxy-5-(3-methoxyphenoxy)pentyl]methanesulfonamido}-cis-hept-5-enoic acid
9. 7-{N-[4-hydroxy-5-(3-fluorophenoxy)pentyl]methanesulfonamido}-cis-hept-5-enoic acid
10. 7-{N-[4-hydroxy-5-(2,3-difluorophenoxy)pentyl]methanesulfonamido}-cis-hept-5-enoic acid
11. 7-{N-[4-hydroxy-5-(3,4-methylenedioxyphenoxy)-pentyl]-methanesulfonamido}-cis-hept-5-enoic acid
12. 7-{N-[4-hydroxy-5-(2,4-dichlorophenoxy)pentyl]-methanesulfonamido}-cis-hept-5-enoic acid

EXAMPLE 4

Preparation of
4-{N-[4-hydroxy-5-(4-fluorophenoxy)pentyl]-methanesulfonamido}butoxyacetic Acid The synthesis of this compound is carried out as described in Example 2 except that, in Step I, the methyl 7-bromo-5-heptynoate is replaced by an equimolar amount of ethyl 4-iodobutoxyacetate. The product of Step I is thus ethyl{4-N-[4-acetoxy-5-(4-fluorophenoxypentyl]-methanesulfonamido}butoxyacetate. The subsequent hydrolysis step yields 4-{N-[4-hydroxy-5-(4-fluorophenoxy)pentyl]-methanesulfonamido}butoxyacetic acid.

EXAMPLE 5

Preparation of
7-{N-[4-hydroxy-5-(4-fluorophenoxy)-2-pentynyl]methanesulfonamido}heptanoic Acid Step A: Preparation of 4-Acetoxy-5-(4-fluorophenoxy)-2-pentyn-1-ol This compound is prepared by the procedure described in Example 2, Step E, except that 1-(2-tetrahydropyranyloxy)-4-acetoxy-5-(4-fluorophenoxy)-2-pentyne (Example 2, Step C) is substituted for 1-(2-tetrahydropyranyloxy)-4-acetoxy-5-(4-fluorophenoxy)-pentane. The subject compound is obtained as a light yellow oil which is not distilled but used directly in the next step.

Step B: Preparation of 4-Acetoxy-1-bromo-5-(4-fluorophenoxy)-2-pentyne

Phosphorus tribromide (10.6 g., 0.039 mole) is added dropwise during 15 minutes to a solution of 4-acetoxy-5-(4-fluorophenoxy)-2-pentyn-1-ol (25.1 g., 0.1 mole) in ether (80 ml.). The resulting solution is stirred at room temperature for 1 hour and then heated at reflux for 30 minutes. The solution is poured into ice water (100 ml.). The organic layer is separated, washed with water, and dried over sodium sulfate. The solvent is evaporated under reduced pressure to leave the title compound as a light yellow oil.

Step C: Preparation of N-[4-acetoxy-5-(4-fluorophenoxy)-2-pentynyl]methanesulfonamide This compound is prepared by the procedure described in Example 2, Step H, except that 4-acetoxy-1-bromo-5-(4-fluorophenoxy)-2-pentyne is substituted for the 4-acetoxy-5-(4-fluorophenoxy)-1-iodopentane. The subject compound is obtained as a pale yellow oil.

Step D: Preparation of 7-{N-[4-hydroxy-5-(4-fluorophenoxy)-2-pentynyl]methanesulfonamido}heptanoic acid This compound is prepared by the procedure described in Example 2, Step I, except that N-[4-acetoxy-5-(4-fluorophenoxy)-2-pentynyl]methanesulfonamide is substituted for the N-[4-acetoxy-5-(4-fluorophenoxy)pentyl]methanesulfonamide and ethyl 7-bromoheptanoate is substituted for ethyl 7-bromo-5-heptynoate. The product is thus ethyl 7-{N-[4-acetoxy-5-(4-fluorophenoxy)-2-pentynyl]methanesulfonamide}-heptanoate. The subsequent hydrolysis (Example 2, Step J) affords the subject compound.

EXAMPLE 6

Preparation of
7-{N-[4-hydroxy-5-(4-fluorophenoxy)-trans-2-pentenyl]methanesulfonamido}heptanoic acid Step A: Preparation of 1-(2-Tetrahydropyranyloxy)-4-hydroxy-5-(4-fluorophenoxy)-2-pentyne To the Grignard reagent prepared from magnesium (12.2 g., 0.5 mole) and bromoethane (54.5 g., 0.5 mole) in tetrahydrofuran (400 ml.) is added, dropwise, during 30 minutes, a solution of tetrahydro-2-(2-propynyloxy)-2H-pyran (67.3 g., 0.5 mole) in tetrahydrofuran (50 ml.). The mixture is stirred at room temperature for 1 hour and then treated, dropwise, during 1 hour with 4-fluorophenoxyacetaldehyde (61.6 g., 0.4 mole). The resulting mixture is heated at reflux for 1 hour, then cooled and poured into an ice-cold saturated solution of ammonium chloride in water.

The organic layer is separated, diluted with ether, washed with water and brine, and dried over magnesium sulfate. The solvents are removed under vacuum to give the title compound as a yellow residual oil.

Step B: Preparation of 1-(2-Tetrahydropyranyloxy)-4-hydroxy-5-(4-fluorophenoxy)-trans-2-pentene Lithium aluminum hydride (7.6 g., 0.2 mole) is dissolved in ether (225 ml.) and 1-(2-tetrahydropyranyloxy)-4-hydroxy-5-(4-fluorophenoxy)-2-pentyne (35.2 g., 0.12 mole) is added dropwise with stirring during 1.5 hour. The resulting mixture is stirred at 25° for 21 hours and then heated at reflux for 4 hours. The mixture is cooled and treated dropwise with ethyl acetate to consume excess lithium aluminum hydride. It is then poured into 600 ml. of ice-cold 20% aqueous potassium hydroxide solution. The oily product is taken up in ether, washed with water and brine, and dried over magnesium sulfate. Removal of solvent under vacuum leaves the title compound as a yellow residual oil.

Step C: Preparation of 1-(2-Tetrahydropyranyloxy)-4-acetoxy-5-(4-fluorophenoxy)-trans-2-pentene A mixture of 1-(2-tetrahydropyranyloxy)-4-hydroxy-5-(4-fluorophenoxy)-trans-2-pentene (23.6 g., 0.08 mole), acetic anhydride (9.2 g., 0.09 mole), and pyridine (7.9 g., 0.1 mole) is heated at 55°–60° for 4 hours and then at 95° for an additional 4 hours. The solution is cooled, diluted with ether and washed with ice-cold saturated sodium carbonate solution, ice water (3×) and brine, and dried over sodium sulfate. Removal of solvent under vacuum leaves the title compound as a residual orange oil.

Step D: Preparation of 4-Acetoxy-5-(4-fluorophenoxy)-trans-2-penten-1-ol

The synthesis of this compound is carried out by the procedure of Example 2, Step E except that an equivalent quantity of 1-(2-tetrahydropyranyloxy)-4-acetoxy-5-(4-fluorophenoxy)-trans-2-pentene is substituted for the 1-(2-tetrahydropyranyloxy)-4-acetoxy-5-(4-fluorophenoxy)-pentane of Example 2, Step E. The product is obtained as a viscous oil.

Step E: Preparation of 4-Acetoxy-5-(4-fluorophenoxy)-trans-2-penten-1-ol Tosylate The synthesis of this compound is carried out by the procedure of Example 2, Step F except than an equivalent quantity of 4-acetoxy-5-(4-fluorophenoxy)-trans-2-penten-1-ol is substituted for the 4-acetoxy-5-(4-fluorophenoxy)-1-pentanol of Example 2, Step F.

Step F: Preparation of 4-Acetoxy-5-(4-fluorophenoxy)-1-iodo-trans-2-pentene

The synthesis of this compound is carried out by the procedure of Example 2, Step G except that an equivalent quantity of 4-acetoxy-5-(4-fluorophenoxy)-trans-2-penten-1-ol tosylate is substituted for the 4-acetoxy-5-(4-fluorophenoxy)-1-pentanol tosylate of Example 2, Step G.

Step G: Preparation of N-[4-acetoxy-5-(4-fluorophenoxy)-trans-2-pentenyl]methanesulfonamide This compound is prepared by the procedure described in Example 2, Step H, except that the 4-acetoxy-5-(4-fluorophenoxy)-1-iodopentane is replaced by an equimolar amount of 4-acetoxy-5-(4-fluorophenoxy)-1-iodotrans-2-pentene. The subject compound is obtained as a viscous oil.

Step H: Preparation of 7-{N-[4-hydroxy-5-(4-fluorophenoxy)-trans-2-pentenyl]methanesulfonamido}heptanoic Acid This compound is prepared by the procedure described in Example 2, Step I, except that N-[4-acetoxy-5-(4-fluorophenoxy)trans-2-pentenyl]methanesulfonamide is substituted for the N-[4-acetoxy-5-(4-fluorophenoxy)pentyl]-methanesulfonamide and ethyl 7-bromoheptanoate is substituted for ethyl 7-bromo-5-heptynoate. The product is thus ethyl 7-{N-[4-acetoxy-5-(4-fluorophenoxy)trans-2-pentenyl]-methanesulfonamido}heptanoate. The subsequent hydrolysis (Example 2, Step J) affords the subject compound.

EXAMPLE 7

Preparation of
7-{N-[4-Hydroxy-5-(4-fluorophenoxy)trans-2-pentenyl]methanesulfonamido}-cis-hept-5-enoic Acid This compound is prepared by the procedure described in Example 2, Step I, except that the N-[4-acetoxy-5-(4-fluorophenoxy)pentyl]methanesulfonamide is replaced by an equimolar amount of N-[4-acetoxy-5-(4-fluorophenoxy)trans-2-pentenyl]methanesulfonamide (Example 6, Step G). This product is thus methyl 7-{N-[4-acetoxy-5-(4-fluorophenoxy)-trans-2-pentenyl]-methanesulfonamido}hept-5-ynoate. The subsequent hydrolysis is carried out as described in Example 2, Step J and affords 7-{N-[4-hydroxy-5-(4-fluorophenoxy)trans-2-pentenyl]methanesulfonamido}hept-5-ynoic acid. The hydrogenation is carried out by the procedure described in Example 3 and affords the subject compound.

EXAMPLE 8

Preparation of
7-{N-[4-Hydroxy-5-(2-fluorophenoxy)pentyl]-methanesulfonamido}heptanoic Acid The synthesis of this compound is carried out as described in Example 1 except that, in Step D, the p-fluorophenol is replaced by an equimolar amount of o-fluorophenol. The product of Step D is thus ethyl 7-{N-[4-hydroxy-5-(2-fluorophenoxy)pentyl]methanesulfonamido}heptanoate.

Anal. Calcd. for $C_{21}H_{34}FNO_6S$: C, 56.35; H, 7.66; N, 3.13; Found: C, 56.80; H, 7.66; N, 2.95.

The subsequent hydrolysis step (as in Example 1, Step E), yields 7-{N-[4-hydroxy-5-(2-fluorophenoxy)-pentyl]-methanesulfonamido}heptanoic acid (E).

Anal. Calcd. for $C_{19}H_{30}FNO_6S$: C, 54.40; H, 7.21; N, 3.34; Found: C, 54.29; H, 7.17; N, 3.05.

EXAMPLE 9

Preparation of
7-{N-[4-Hydroxy-5-(3-trifluoromethylphenoxy)-pentyl]methanesulfonamido}heptanoic Acid The synthesis of this compound is carried out as described in Example 1 except that, in Step D, the p-fluorophenol is replaced by an equimolar amount of 3-trifluoromethylphenol. The product of Step D is thus ethyl 7-{N-[4-hydroxy-5-(3-trifluoromethylphenoxy)-pentyl]-methanesulfonamido}heptanoate. The subsequent hydrolysis step yields 7-{N-[4-hydroxy-5-(3-trifluoromethylphenoxy)-pentyl]-methanesulfonamido}heptanoic acid (E).

EXAMPLE 10

Preparation of
7-{N-[4-Hydroxy-5-(3-chlorophenoxy)pentyl]-methanesulfonamido}heptanoic Acid Hydrate The synthesis of this compound is carried out as described in Example 1 except that, in Step D, the p-fluorophenol is replaced by an equimolar amount of 3-chlorophenol. The product of Step D is thus ethyl 7-{N-[4-hydroxy-5-(3-chlorophenoxy)pentyl]methanesulfonamido}-heptanoate.

Anal. Calcd. for $C_{21}H_{34}ClNO_6S$: C, 54.35; H, 7.39; N, 3.02; Found: C, 53.81; H, 7.44; N, 2.90.

The subsequent step yields 7-{N-[4-hydroxy-5-(3-chlorophenoxy)pentyl]methanesulfonamido}heptanoic acid hydrate (E).

Anal. Calcd. for $C_{19}H_{30}ClNO_6S \cdot H_2O$: C, 50.26; H, 7.11; N, 3.09; Found: C, 50.05; H, 6.74; N, 3.46.

EXAMPLE 11

Preparation of
7-{N-[4-Hydroxy-5-(4-methoxyphenoxy)pentyl]-methanesulfonamido}heptanoic Acid Hemi-hydrate The synthesis of this compound is carried out as described in Example 1 except that, in Step D, the p-fluorophenol is replaced by an equimolar amount of p-methoxyphenol. The product of Step D is thus ethyl 7-{N-[4-hydroxy-5-(4-methoxyphenoxy)pentyl]methanesulfonamido}-heptanoate. The subsequent step yields 7-{N-[4-hydroxy-5-(4-methoxyphenoxy)pentyl]methanesulfonamido}heptanoic acid hemi-hydrate (E).

Anal. Calcd. for $C_{20}H_{33}NO_7S \cdot \frac{1}{2}H_2O$: C, 54.52; H, 7.78; N, 3.18; Found: C, 54.60; H, 8.01; N, 3.17.

EXAMPLE 12

Preparation of
7-[N-(4-Hydroxy-5-phenoxypentyl)methanesulfonamido]heptanoic Acid Hemi-hydrate The synthesis of this compound is carried out as described in Example 1 except that, in Step D, the p-fluorophenol is replaced by an equimolar amount of phenol. The product of Step D is thus ethyl 7-[N-(4-hydroxy-5-phenoxypentyl)methanesulfonamido]heptanoate.

Anal. Calcd. for $C_{21}H_{35}NO_6S$: C, 58.71; H, 8.21; N, 3.26; Found: C, 58.59; H, 8.34; N, 3.15.

The subsequent hydrolysis step yields 7-[N-(4-hydroxy-5-phenoxypentyl)methanesulfonamido]heptanoic acid hemi-hydrate (E).

Anal. Calcd. for $C_{19}H_{31}NO_6S \cdot \frac{1}{2}H_2O$: C, 55.59; H, 7.86; N, 3.41; Found: C, 55.70; H, 7.86; N, 3.30.

Further, following the procedure of Example 1, Step D, but substituting for the p-fluorophenol used therein an equivalent quantity of
1. 3-bromophenol
2. 3-iodophenol
3. 2-chlorophenol
4. 3-methylphenol
5. 3-mesylphenol
6. 3-dimethylaminophenol
7. 3-ethylphenol
8. 3-methoxyphenol
9. 3-acetylphenol
10. 3-nitrophenol
11. 3-fluorophenol
12. 2,3-difluorophenol
13. 3,4-methylenedioxyphenol
or
14. 2,4-dichlorophenol and conducting the reaction and isolation as described, the product isolated in each instance is
1. ethyl 7-{N-[4-hydroxy-5-(3-bromophenoxy)pentyl]-methanesulfonamido}heptanoate
2. ethyl 7-{N-[4-hydroxy-5-(3-iodophenoxy)pentyl]-methanesulfonamido}heptanoate
3. ethyl 7-{N-[4-hydroxy-5-(2-chlorophenoxy)pentyl]-methanesulfonamido}heptanoate
4. ethyl 7-{N-[4-hydroxy-5-(3-methylphenoxy)pentyl]-methanesulfonamido}heptanoate
5. ethyl 7-{N-[4-hydroxy-5-(3-mesylphenoxy)pentyl]-methanesulfonamido}heptanoate
6. ethyl 7-{N-[4-hydroxy-5-(3-dimethylaminophenoxy)pentyl]-methanesulfonamido}heptanoate
7. ethyl 7-{N-[4-hydroxy-5-(3-ethylphenoxy)pentyl]-methanesulfonamido}heptanoate
8. ethyl 7-{N-[4-hydroxy-5-(3-methoxyphenoxy)-pentyl]-methanesulfonamido}heptanoate
9. ethyl 7-{N-[4-hydroxy-5-(3-acetylphenoxy)pentyl]-methanesulfonamido}heptanoate
10. ethyl 7-{N-[4-hydroxy-5-$\beta$-nitrophenoxy)pentyl]-methanesulfonamido}heptanoate
11. ethyl 7-{N-[4-hydroxy-5-(3-fluorophenoxy)pentyl]-methanesulfonamido}heptanoate
12. ethyl 7-{N-[4-hydroxy-5-(2,3-difluorophenoxy)-pentyl]-methanesulfonamido}heptanoate
13. ethyl 7-{N-[4-hydroxy-5-(3,4-methylenedioxyphenoxy)-pentyl]methanesulfonamido}heptanoate
14. ethyl 7-{N-[4-hydroxy-5-(2,4-dichlorophenoxy)-pentyl]-methanesulfonamido}heptanoate Following the procedure of Example 1, Step E, but substituting for the ethyl 7- N-[4-hydroxy-5-(4-fluorophenoxy)-pentyl]methanesulfonamido heptanoate used therein an equivalent amount of each of the 14 esters listed above and conducting the reaction and isolation as described, there are obtained:
1. 7-{N-[4-hydroxy-5-(3-bromophenoxy)pentyl]methanesulfonamido}heptanoic acid
2. 7-{N-[4-hydroxy-5-(3-iodophenoxy)pentyl]methanesulfonamido}heptanoic acid
3. 7-{N-[4-hydroxy-5-(2-chlorophenoxy)pentyl]methanesulfonamido}heptanoic acid
4. 7-{N-[4-hydroxy-5-(3-methylphenoxy)pentyl]methanesulfonamido}heptanoic acid
5. 7-{N-[4-hydroxy-5-(3-mesylphenoxy)pentyl]methanesulfonamido}heptanoic acid
6. 7-{N-[4-hydroxy-5-(3-dimethylaminophenoxy)pentyl]-methanesulfonamido}heptanoic acid
7. 7-{N-[4-hydroxy-5-(3-ethylphenoxy)pentyl]methanesulfonamido}heptanoic acid
8. 7-{N-[4-hydroxy-5-(3-methoxyphenoxy)pentyl]methanesulfonamido}heptanoic acid
9. 7-{N-[4-hydroxy-5-(3-acetylphenoxy)pentyl]methanesulfonamido}heptanoic acid
10. 7-{N-[4-hydroxy-5-(3-nitrophenoxy)pentyl]methanesulfonamido}heptanoic acid
11. 7-{N-[4-hydroxy-5-$\beta$-fluorophenoxy)pentyl]methanesulfonamido}heptanoic acid
12. 7-{N-[4-hydroxy-5-(2,3-difluorophenoxy)pentyl]-methanesulfonamido}heptanoic acid
13. 7-{N-[4-hydroxy-5-(3,4-methylenedioxyphenoxy)-pentyl]-methanesulfonamido}heptanoic acid
14. 7-{N-[4-hydroxy-5-(2,4-dichlorophenoxy)pentyl]-methanesulfonamido}heptanoic acid

EXAMPLE 13

Preparation of
7-[N-(4-Hydroxy-5-benzyloxypentyl)methanesulfonamido]heptanoic Acid Hemi-Hydrate The synthesis of this compound is carried out as described in Example 1 except that, in Step D, the p-fluorophenol is replaced by an equimolar amount of benzyl alcohol. The product of Step D is thus ethyl 7-[N-(4-hydroxy-5-benzyloxypentyl)methanesulfonamido]heptanoate. The subsequent hydrolysis step yields 7-[N-(4-hydroxy-5-benzyloxypentyl)methanesulfonamido]heptanoic acid hemihydrate (E).

Anal. Calcd. for $C_{20}H_{33}NO_6S\cdot\frac{1}{2}H_2O$: C, 56.58; H, 8.07; N, 3.30; Found: C, 56.49; H, 7.78; N, 3.23.

EXAMPLE 14

Preparation of 7-[N-(4-Hydroxy-5-furfuryloxypentyl)methanesulfonamido]heptanoic Acid Hemi-Hydrate The synthesis of this compound is carried out as described in Example 1 except that, in Step D, the p-fluorophenol is replaced by an equimolar amount of furfuryl alcohol. The product of Step D is thus ethyl 7-[N-(4-hydroxy-5-furfuryloxypentyl)methanesulfonamido]heptanoate. The subsequent step yields 7-[N-(4-hydroxy-5-furfuryloxypentyl)methanesulfonamido]heptanoic acid hemi-hydrate (E).

Anal. Calcd. for $C_{18}H_{31}NO_7S\cdot\frac{1}{2}H_2O$: C, 52.15; H, 7.78; N, 3.25; Found: C, 52.31; H, 7.42; N, 3.04.

EXAMPLE 15

Preparation of 7-{N-[4-Hydroxy-5-(3-pyridyloxy)pentyl]-methanesulfonamido}heptanoic Acid The synthesis of this compound is carried out as described in Example 1 except that, in Step D, the p-fluorophenol is replaced by an equimolar amount of 3-hydroxypyridine. The product of Step D is thus ethyl 7-{N-[4-hydroxy-5-(3-pyridyloxy)pentyl]methanesulfonamido}heptanoate. The subsequent step yields 7-{N-[4-hydroxy-5-(3-pyridyloxy)-pentyl]methanesulfonamido}heptanoic acid (E).

EXAMPLE 16

Preparation of 7-{N-[4-Hydroxy-5-(5-pyrimidyloxy)pentyl]-methanesulfonamido}heptanoic Acid The synthesis of this compound is carried out as described in Example 1 except that, in Step D, the p-fluorophenol is replaced by an equimolar amount of 5-hydroxypyrimidine. The product of Step D is thus ethyl 7-{N-[4-hydroxy-5-(5-pyrimidyloxy)pentyl]methanesulfonamido}heptanoate. The subsequent step yields 7-{N-[4-hydroxy-5-(5-pyrimidyloxy)-pentyl]methanesulfonamido}heptanoic acid (E).

EXAMPLE 17

Preparation of 7-[N-(4-Hydroxy-5-phenylthiopentyl)-methanesulfonamido]heptanoic Acid The synthesis of this compound is carried out as described in Example 1 except that, in Step D, the p-fluorophenol is replaced by an equimolar amount of thiophenol. The product of Step D is thus ethyl 7-[N-(4-hydroxy-5-phenylthiopentyl)methanesulfonamido]heptanoate.

Anal. Calcd. for $C_{21}H_{35}NO_5S_2$: C, 56.60; H, 7.92; N, 3.14; Found: C, 56.40; H, 8.11; N, 3.11.

The subsequent step yields 7-[N-(4-hydroxy-5-phenylthiopentyl)methanesulfonamido]heptanoic acid (E).

Anal. Calcd. for $C_{19}H_{31}NO_5S_2$: C, 54.65; H, 7.48; N, 3.36; Found: C, 54.02; H, 7.75; N, 3.31.

EXAMPLE 18

Preparation of 7-{N-[4-Hydroxy-5-(4-fluorophenylthio)pentyl]-methanesulfonamido}heptanoic Acid The synthesis of this compound is carried out as described in Example 1 except that, in Step D, the p-fluorophenol is replaced by an equimolar amount of 4-fluorothiophenol. The product of Step D is thus ethyl 7-{N-[4-hydroxy-5-(4-fluorophenylthio)pentyl]methanesulfonamido}-heptanoate.

Anal. Calcd. for $C_{21}H_{34}FNO_5S_2$: C, 54.40; H, 7.39; N, 3.02; Found: C, 54.26; H, 7.27; N, 2.83.

The subsequent step yields 7-{N-[4-hydroxy-5-(4-fluorophenylthio)pentyl]methanesulfonamido}heptanoic acid (E).

Anal. calcd. for $C_{19}H_{30}FNO_5S_2$: C, 52.39; H, 6.94; N, 3.22; Found: C, 51.98; H, 6.85; N, 3.00.

EXAMPLE 19

Preparation of 7-[N-(4-Hydroxy-5-ethoxypentyl)methanesulfonamido]heptanoic Acid

To a solution of ethyl 7-[N-(4,5-epoxypentyl)-methanesulfonamido]heptanoate (7.0 g., 0.02 mole) in ethanol (150 ml.) is added sodium hydroxide (1.84 g., 0.046 mole) dissolved in water (15 ml.). This solution is stirred at room temperature for 18 hours, then concentrated to one-half volume under reduced pressure. Water (150 ml.) is added and this aqueous solution is extracted with ether (2 × 100 ml.). The aqueous layer is then acidified (dilute hydrochloric acid) and extracted with ethyl acetate (2 × 150 ml.). The organic phase is washed with brine, dried over sodium sulfate, then evaporated in vacuo. The yield of subject compound is 4.0 g. (54%) of pale yellow oil.

Anal. Calcd. for $C_{15}H_{31}NO_6S$: C, 50.97; H, 8.84; N, 3.96; Found: C, 50.31; H, 8.74; N, 3.95.

Further, following the procedure of this example but substituting for the ethanol used above an equivalent amount of 1. 1-propanol
2. 1-butanol
3. sec. butyl alcohol
4. 3,3,3-trifluoro-1-propanol or 5. propylmercaptan there is obtained:

1. 7-[N-(4-hydroxy-5-propoxypentyl)methanesulfonamido]-heptanoic acid
2. 7-[N-(4-hydroxy-5-butoxypentyl)methanesulfonamido]-heptanoic acid
3. 7-{N-[4-hydroxy-5-(2-methylpropoxy)pentyl]methanesulfonamido}heptanoic acid
4. 7-{N-[4-hydroxy-5-(3,3,3-trifluoropropoxy)pentyl]-methanesulfonamido}heptanoic acid
5. 7-[N-(4-hydroxy-5-propylthiopentyl)methanesulfonamido]-heptanoic acid

EXAMPLE 20

Preparation of Methyl 7-{N-[4-Hydroxy-5-(4-fluorophenoxy)-pentyl]methanesulfonamido}heptanoate A solution of diazomethane (approximately 2.5 g., 0.06 mole) in ether (100 ml.) is mixed with a solution of 7-{N-[4-hydroxy-5-(4-fluorophenoxy)pentyl]methanesulfonamido}heptanoic acid (12.3 g., 0.03 mole) (Example 1, Step E) in ether (50 ml.). The resulting solution is allowed to stand at room temperature for 4 hours. Acetic acid is then added to destroy the excess diazomethane and the solution is washed with dilute sodium bicarbonate solution and water and dried over sodium sulfate. Evaporation of volatile materials at reduced pressure yields methyl 7-{N-[4-hydroxy-5-(4-fluorophenoxy)pentyl]methanesulfonamido}heptanoate as a viscous oil.

EXAMPLE 21

Preparation of 7-{N-[4-Acetoxy-5-(4-fluorophenoxy)pentyl]-methanesulfonamido}heptanoic Acid A mixture of 7-{N-[4-hydroxy-5-(4-fluorophenoxy)-pentyl]methanesulfonamido}heptanoic acid (12.3 g., 0.03 mole) (Example 1, Step E) and acetic anhydride (6.1 g., 0.06 mole) is kept at room temperature for 18 hours. This mixture is taken up in 80 ml. of ethyl ether. The solution is extracted with an ice-cold solution of 8 g. of sodium hydroxide in 150 ml. of water. The basic solution is separated and acidified with concentrated hydrochloric acid. The crude product that separates is extracted into ether, washed with water and dried over sodium sulfate. The ether is evaporated and the residual oil is purified by chromatography on silica gel using 2% methanol in chloroform as the eluting solvent. There is obtained 7-{N-[4-acetoxy-5-(4-fluorophenoxy)pentyl]methanesulfonamido}-heptanoic acid as a viscous oil.

EXAMPLE 22

Preparation of N-[(2-dimethylamino)ethyl]-7-{N-[4-hydroxy-5-(4-fluorophenoxy)pentyl]methanesulfonamido}heptanamide A solution of 7-{N-[4-hydroxy-5-(4-fluorophenoxy)-pentyl]methanesulfonamido}heptanoic acid (4.19 g., 0.01 mole) (Example 1, Step E), triethylamine (1.74 ml., 0.0125 mole) and distilled water (18 ml.) in acetonitrile (100 ml.) is treated with N-t-butyl-5-methylisoxazolium perchlorate (3.0 g., 0.0125 mole). The resulting solution is evaporated in vacuo at 20°–25° C. over 4 hours providing a tacky residue which is triturated with water (150 ml.) at 0°–5° C. for 15 minutes. After decanting the aqueous phase, the oily residue is dissolved in benzene-ether [(1:1), 200 ml.]. The organic extract is dried over sodium sulfate, then evaporated in vacuo providing the desired "active ester".

A solution of 2-dimethylaminoethylamine (0.88 g., 0.01 mole) in acetonitrile (25 ml.) is added to a solution of the "active ester" in acetonitrile (25 ml.) and the solution is stirred at room temperature for 17 hours. The solvent is removed in vacuo, the residual oil is partitioned between ether (200 ml.) and water (200 ml.). The ether layer is extracted with 5% hydrochloric acid (2 × 50 ml.). The aqueous acid phase is made basic with aqueous sodium carbonate then extracted with ether. The ether extract is washed with brine solution, dried over sodium sulfate, evaporated in vacuo leaving the N-[(2-dimethylamino)ethyl]-7-{N-[4-hydroxy-5-(4-fluorophenoxy)pentyl]methanesulfonamido}heptanamide.

What is claimed is:
1. The compound of the formula

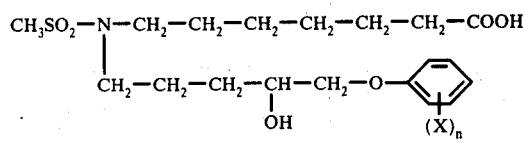

wherein X is hydrogen, halogen, trifluoromethyl, loweralkyl, or loweralkoxy; and n is 1 or 2.

2. The compound of claim 1 which is 7-{N-[4-hydroxy-5-(4-fluorophenoxy)pentyl]methanesulfonamido}-heptanoic acid.

3. The compound of claim 1 which is 7-{N-[4-hydroxy-5-(2-fluorophenoxy)pentyl]methanesulfonamido}-heptanoic acid.

4. The compound of claim 1 which is 7-{N-[4-hydroxy-5-(3-trifluoromethylphenoxy)pentyl]methanesulfonamido}heptanoic acid.

5. The compound of claim 1 which is 7-{N-[4-hydroxy-5-(3-chlorophenoxy)pentyl]methanesulfonamido}-heptanoic acid.

6. The compound of claim 1 which is 7-{N-[4-hydroxy-5-(4-methoxyphenoxy)pentyl]methanesulfonamido}-heptanoic acid.

7. The compound of claim 1 which is 7-[N-(4-hydroxy-5-phenoxypentyl)methanesulfonamido]heptanoic acid.

8. The compound of claim 1 wherein X is selected from bromo, iodo, chloro, methyl, ethyl, methoxy, fluoro, difluoro, and dichloro.

* * * * *